US006781388B2

(12) United States Patent
Wang et al.

(10) Patent No.: US 6,781,388 B2
(45) Date of Patent: Aug. 24, 2004

(54) LIQUID PROPERTY SENSOR

(75) Inventors: Da Yu Wang, Troy, MI (US); Ying Jie Lin, El Paso, TX (US); David K. Lambert, Sterling Heights, MI (US)

(73) Assignee: Delphi Technologies, Inc., Troy, MI (US)

(*) Notice: Subject to any disclaimer, the term of this patent is extended or adjusted under 35 U.S.C. 154(b) by 213 days.

(21) Appl. No.: 09/963,862

(22) Filed: Sep. 26, 2001

(65) Prior Publication Data

US 2003/0057968 A1 Mar. 27, 2003

(51) Int. Cl.[7] ............................................. G01R 27/26
(52) U.S. Cl. ..................... 324/690; 324/663; 324/688
(58) Field of Search .................................. 324/690, 663, 324/664, 679, 686, 688; 73/118.1

(56) References Cited

U.S. PATENT DOCUMENTS

| | | | |
|---|---|---|---|
| 3,826,979 A | * 7/1974 | Steinmann | ................. 361/178 |
| 5,795,545 A | 8/1998 | Koripella et al. | ............. 422/94 |
| 6,222,376 B1 | * 4/2001 | Tenney, III | ................. 324/664 |
| 6,275,048 B1 | 8/2001 | Milli | ......................... 324/690 |
| 6,564,624 B2 | 5/2003 | Lin et al. | ................... 73/118.1 |

* cited by examiner

Primary Examiner—Albert Decady
Assistant Examiner—James Kerveros
(74) Attorney, Agent, or Firm—Jimmy L. Funke

(57) ABSTRACT

A sensor includes a substrate consisting essentially of a non-conductive material, a first electrode, and a second electrode disposed on a first surface of the substrate, wherein the first electrode includes a first major portion traversing a length of the substrate and a finger extending from the major portion, wherein the second electrode includes a second major portion traversing the length of the substrate and a finger extending from the second major portion, wherein the first electrode finger extends toward the second electrode major portion and the second electrode finger extends toward the first electrode major portion and is substantially parallel to the first finger, and a third electrode connected to a ground, wherein the third electrode is interposed between and about the first and second electrodes.

17 Claims, 5 Drawing Sheets

LIQUID PROPERTY SENSOR

BACKGROUND OF THE INVENTION

Automotive systems continuously or periodically monitor numerous fluids to ensure that performance continues as expected. There are many fluid properties that can be monitored using techniques such as compositional analysis, quantitative analysis and contaminant concentration. Examples of these include monitoring for excess soot in lubricant oil, for the presence of water or methanol in gasoline, for the remaining quantity of lubricant, and the like.

The measurement of capacitance or complex impedance between two parallel plate electrodes or between two coaxial tube electrodes can be used to quantify certain fluid properties. The fluid is typically passed through a gap maintained by the parallel plates and a dielectric constant of the fluid is determined as it is passed between the plates. Monitoring the fluid's dielectric constant can be used to detect changes in the fluid, indicating the presence of, for example, contaminants or additives. Alternatively, the measured capacitance may be used to determine the level of fluid in a container.

Some previous capacitive sensors of fluid properties have used plastic components to fabricate the sensor. For sensors that include plastic components, the dielectric constant (i.e., complex impedance) is known to be nonlinear as a function of temperature. To compensate for this non-linear behavior, capacitive sensors fabricated with plastic components require additional data collection, which adds to the overall operating and manufacturing costs.

Other types of capacitive sensors use rivets and spacer rings to separate opposing carrier plates. The spacer rings are positioned onto rivet shafts between the plates to form a gap. The rivets and spacer rings must be electrically insulated and are necessarily positioned outside the areas of the metal capacitor coatings or claddings, thereby adding to the overall costs to manufacture the sensor. Moreover, the structural stability of the sensor relies on the number of rivets and the spacing of the rivets from each other. The rivets cannot assure in all instances that the carrier plates will not bend or warp during use. Such warping is undesirable because it varies the spacing between the capacitor plates resulting in variability and error.

To optimize the signal-to-noise ratio for these types of capacitive sensors, the gap (or distance) between the parallel plates needs to be minimized. However, if the gap becomes too small, the fluid flow within the gap is hindered and as a result, the response time of the sensor increases. Moreover, there is a propensity for the gap to trap material and further hinder the fluid flow.

Even if the above noted problems are overcome, it is always a challenge to manufacture a device with a small gap economically and reproducibly.

SUMMARY OF THE INVENTION

A sensor comprising a substrate consisting essentially of a non-conductive material; a first electrode, and a second electrode disposed on a first surface of the substrate, wherein the first electrode comprises a first major portion traversing a length of the substrate and a finger extending from the major portion, wherein the second electrode comprises a second major portion traversing the length of the substrate and a finger extending from the second major portion, wherein the first electrode finger extends toward the second electrode major portion and the second electrode finger extends toward the first electrode major portion and is substantially parallel to the first finger; and a third electrode connected to a ground, wherein the third electrode is interposed between and about the first and second electrodes.

In another embodiment, a sensor for measuring a characteristic of a fluid comprises a first, a second and a third ceramic substrate. A first capacitive sensor is sandwiched between the first and second substrates. The first capacitive sensor comprises a first electrode, a second electrode and a third electrode, wherein a portion of the first and second electrodes form complementary parallel finger pairs and wherein the third electrode is grounded and is interposed between and about the first and second electrodes. A second capacitive sensor is sandwiched between the second and third substrates. The second capacitive sensor comprises a fourth electrode, a fifth electrode and a sixth electrode, wherein a portion of the fourth and fifth electrodes form complementary parallel finger pairs, and wherein the sixth electrode is grounded and is interposed between and about the fourth and fifth electrodes. Circuitry means are connected to the first and second capacitive sensors for producing an output signal based on an electrical field generated by the finger pairs.

A system for detecting a change in fluid properties comprises a power supply, a source circuit and an output circuit. The source circuit includes a sensor, wherein the sensor comprises a substrate consisting essentially of a non-conductive material. A first electrode, and a second electrode are disposed on a first surface of the substrate, wherein the first electrode comprises a first major portion traversing a length of the substrate and a finger extending from the major portion. The second electrode comprises a second major portion traversing the length of the substrate and a finger extending from the second major portion, wherein the first electrode finger extends toward the second electrode major portion and the second electrode finger extends toward the first electrode major portion and is substantially parallel to the first finger. A third electrode is connected to a ground, wherein the third electrode is interposed between and about the first and second electrodes. The output circuit comprises amplification means for amplifying a differential signal to produce an output signal that is proportional to a change in an impedance property of a fluid.

A process for measuring the capacitive properties of a fluid comprises attaching a sensor to a fluid container. The sensor comprises a substrate consisting essentially of a non-conductive material. A first electrode and a second electrode are disposed on a first surface of the substrate, wherein the first electrode comprises a first major portion traversing a length of the substrate and a finger extending from the major portion. The second electrode comprises a second major portion traversing the length of the substrate and a finger extending from the second major portion, wherein the first electrode finger extends toward the second electrode major portion and the second electrode finger extends toward the first electrode major portion and is substantially parallel to the first finger. A third electrode is connected to a ground, wherein the third electrode is interposed between and about the first and second electrodes. The process further includes applying an oscillating voltage source to the first electrode, generating an electrical field between the first electrode finger and the second electrode finger, wherein the electrical field extends into the fluid and monitoring a current passing to the ground from the second electrode.

The above described and other features are exemplified by the following figures and detailed description.

BRIEF DESCRIPTION OF THE DRAWINGS

Referring now to the figures wherein the like elements are numbered alike.

DESCRIPTION OF THE PREFERRED EMBODIMENT

Figure 1:
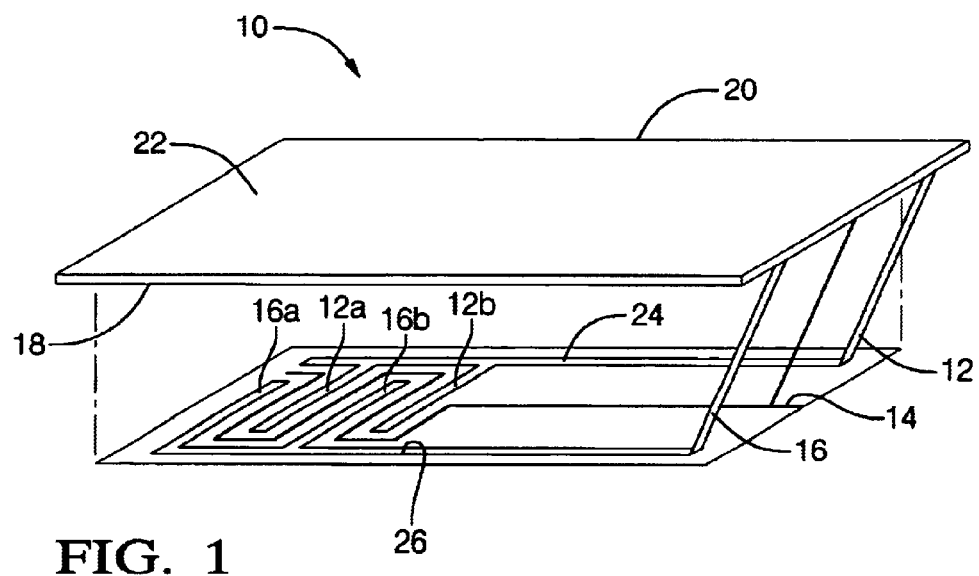
FIG. 1 shows an exploded perspective view of a capacitive sensor.

FIG. 1 illustrates a sensor generally designated by reference numeral 10. The sensor 10 includes three electrodes 12, 14, 16 deposited onto a major surface 18 of a substrate 20. The electrodes 12, 16 are configured to include complementary parallel finger pairs, e.g., 12a and 16a, 12b and 16b, etc. Each of the electrodes 12, 16 includes at least two fingers extending from a major portion 24, 26, respectively, toward the opposing electrode main portion 26, 24, respectively. The fingers 12a, 12b, 16a, 16b, . . . , are preferably disposed substantially parallel to each other and more preferably, substantially perpendicular to the main portions 24, 26. Electrode 14, which is grounded, is interposed between and about electrodes 12, 16 without physically contacting either electrode. Electrode 14 functions as a guard electrode to intercept electrostatic flux passing near the sensor surface 18 from electrodes 12 and 16. With electrode 14 grounded, the flux that passes from electrode 12 to electrode 16, (or vice versa, depending on which electrode functions as the source electrode and which electrode functions as the detection electrode) samples a fluid of interest at a greater distance from surface 18 than those sensors without a guard electrode since electrostatic flux contributions at the sensor surface are minimal or substantially eliminated. A general discussion of capacitive sensors can be found in U.S. application Ser. No. 09/643,236 entitled, "Capacitive Proximity Sensor" to Lambert, incorporated herein by reference in its entirety.

Figure 8:
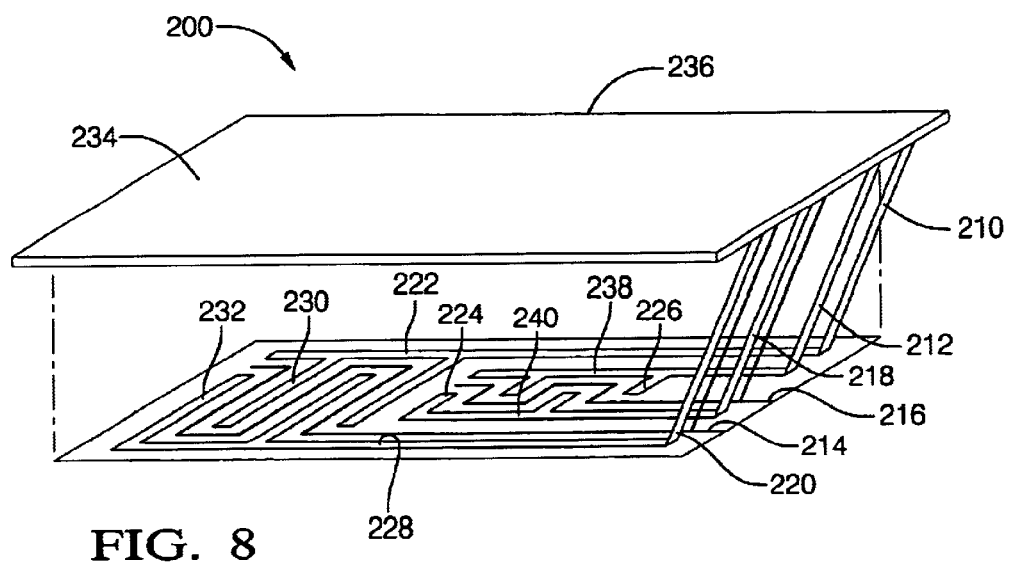
FIG. 8 shows an exploded perspective view of a capacitive sensor in accordance with another embodiment.

To increase sensitivity, the substrate 20 may further include additional electrodes or interdigitated electrodes (an exemplary embodiment is shown in FIG. 8). For example, the substrate 20 may include additional electrodes on the same surface 18 or may include additional electrodes disposed on its ether major surface 22. In this manner, the capacitive sensor 10 comprises numerous individual sensors, wherein the spacing between each successive sensor may be progressively varied. For example, the separation of individual sensors may be small near one amid of the sensor 10 and larger at the other end to provide a finer graduation of sensing of a liquid level as the liquid nears the bottom of a container. For fluid property monitoring, the sensor may include a plurality of tightly spaced electrodes that, in combination, provide an increase in signal to noise ratio and sensitivity.

Figure 2:
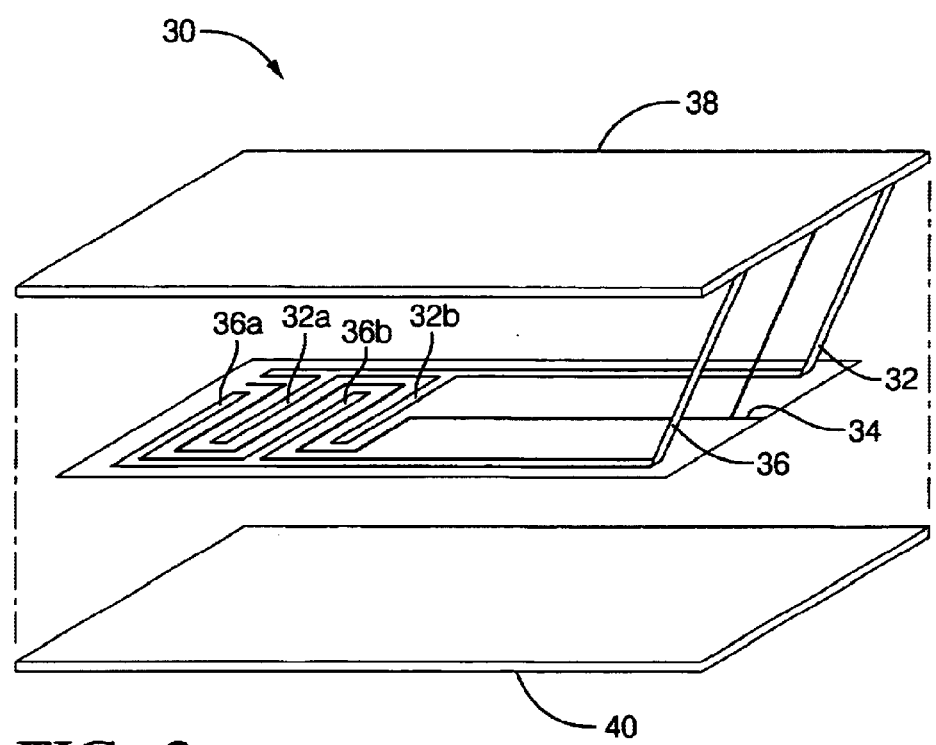
FIG. 2 shows an exploded perspective view of a capacitive sensor in accordance of another embodiment.

Another embodiment is shown in FIG. 2. Here, a capacitive sensor 30 comprises three electrodes 32, 34, and 36, sandwiched between two substrates 38, 40. Similar to FIG. 1, each electrode 32 and 36 includes complementary pairs of parallel fingers, e.g., 32a and 34a, 32b and 34b, etc. The substrates 38, 40 provide support for the electrodes 32, 34 and 36 as well as protection from the fluid or operating environment. The sensors employing multi-layered substrates do not contain a gap that is in communication with the environment about the sensor. That is, there is no separation of the substrates at its joined interface apart from the presence of the electrodes sandwiched between the substrates. Electrode 34 is interposed between and about electrodes 32, 36, and is grounded.

Figure 3:
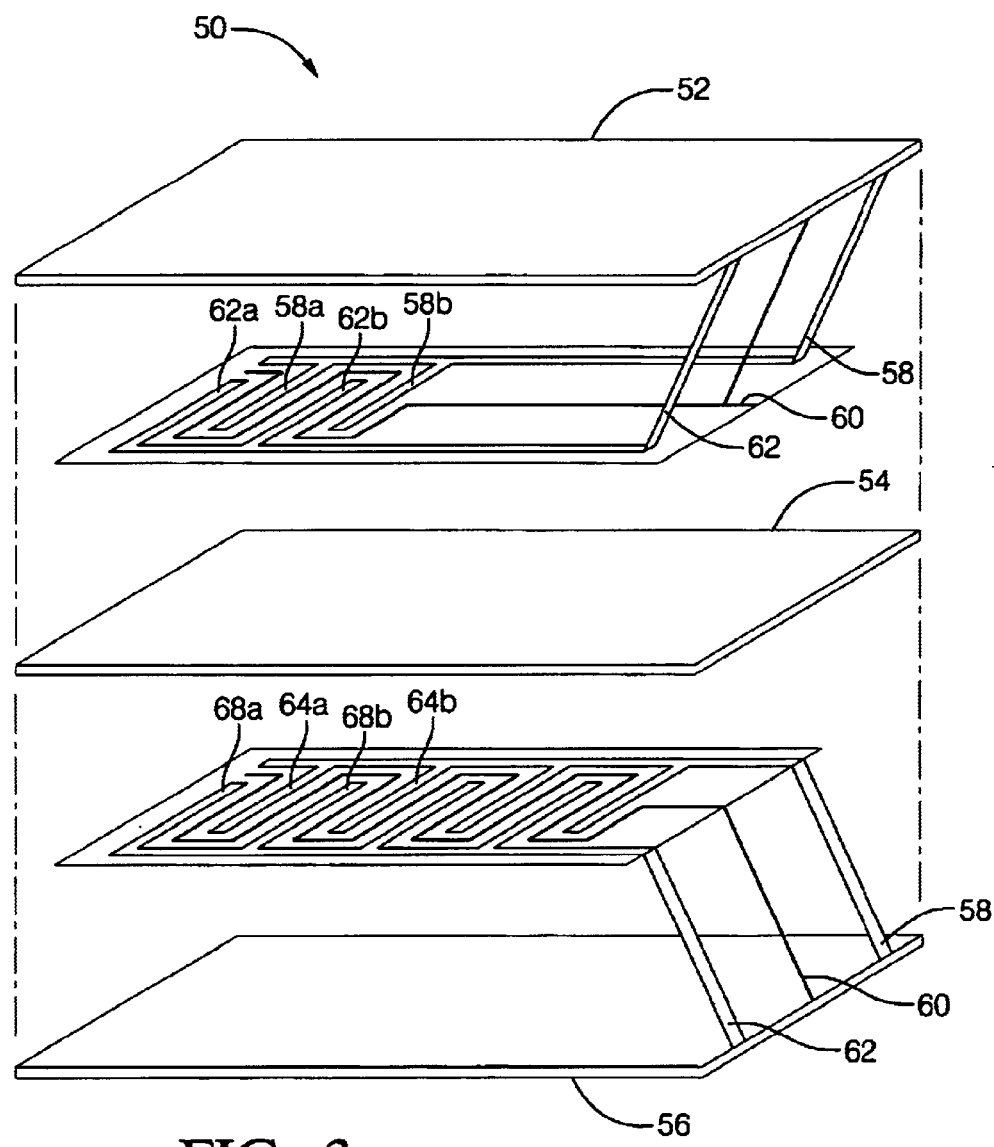
FIG. 3 shows an exploded perspective view of a capacitive sensor in accordance of another embodiment.

FIG. 3 illustrates a sensor 50 configured for dielectric sensing and fluid level sensing. The capacitive sensor 50 includes substrates 52, 54, 56, electrodes 58, 60, 62 sandwiched between substrates 52, 54 and electrodes 64, 66, 68 sandwiched between substrates 54, 56. As will be discussed in further detail below, electrodes 58, 62 are configured for sensing the intrinsic property of the fluid from the measured impedance whereas electrodes 64, 68 are configured for monitoring the fluid level. Electrodes 60 and 66 are interposed between and about the corresponding electrodes as shown and are grounded. Electrodes 60 and 66 function as guard electrodes in the manner previously described.

The electrodes 58, 62 include a plurality of complementary pairs of parallel fingers, e.g., 58a and 62a, 58b and 62b, etc, extending along a portion of the length of the substrate 52. For sensing fluid properties, it is preferred that the fingers be positioned on the substrate to maintain continuous electrical field communication with the fluid of interest for detecting a dielectric change in the fluid properties, e.g., from the presence of contaminants, additives, degradation products or the like. For example, if the fluid to be sensed comprises oil disposed in an oil pan of an automotive vehicle, it is preferred that the electrodes be disposed such that during operation of the motor vehicle, the fingers of the sensor continuously maintain electrical field communication with the oil. In this manner, changes detected by the sensor will not result in false readings due to a failure to maintain constant electrical field communication.

In contrast, the electrodes 64, 68 shown configured for sensing the level of fluid includes a plurality of complementary pairs of parallel fingers, e.g., 64a and 68a, 64b and 68b, etc, extending along a length of the substrate 56. The exact length along the substrate length depends on a number of factors including, but not limited to, the fluid properties, the height of the tank or vessel that contains the fluid, and the like. In this manner, the electrodes can detect a change in the level of fluid, for example, by detecting a dielectric constant of the fluid in the sensor portion submerged in the fluid and a portion that is outside of the fluid, i.e., the space above the level of fluid (air, vapors from the liquid and the like). For example, a signal generated by this type of sensor informs the user of the level of fluid remaining in the tank.

Figure 4:
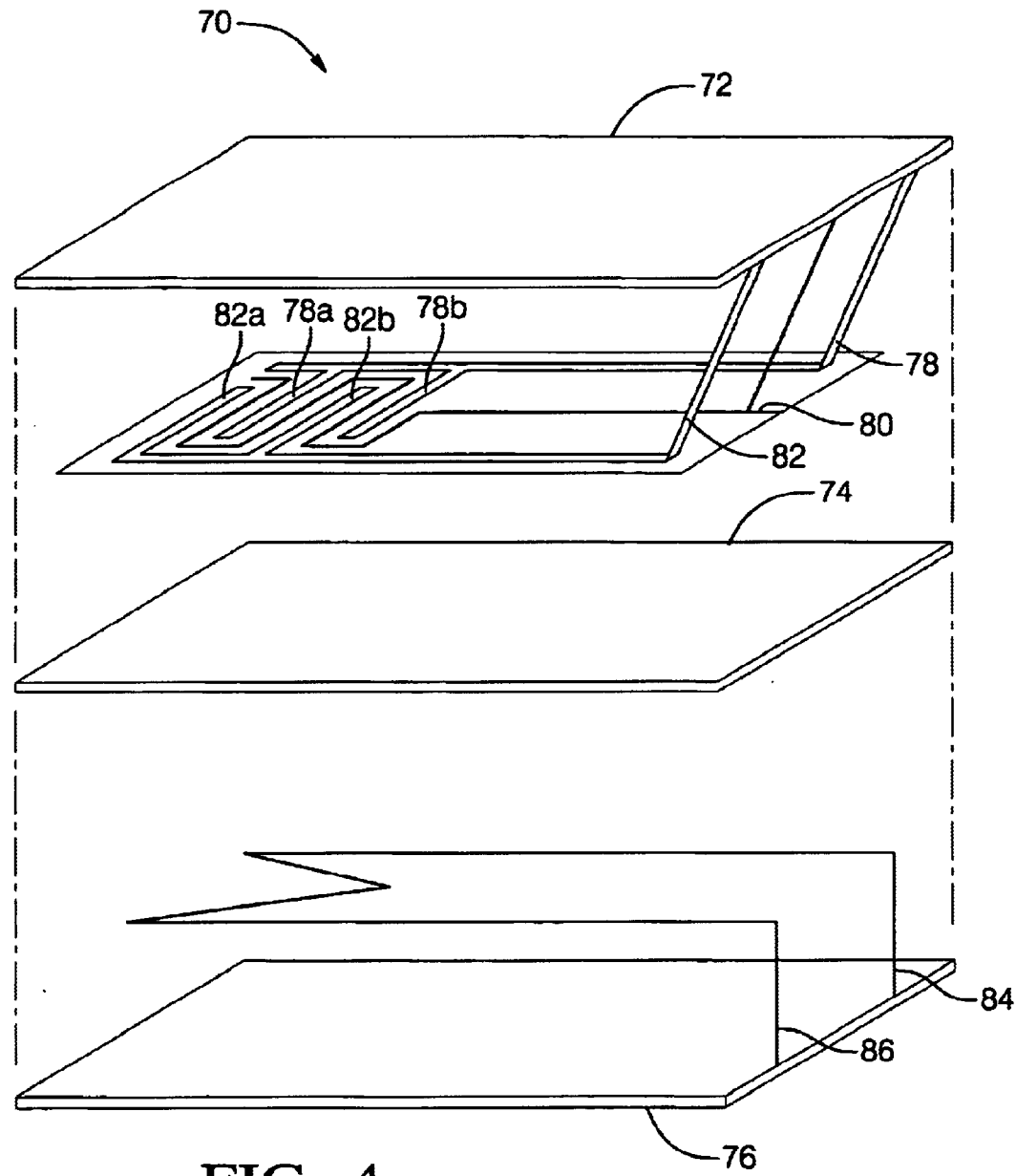
FIG. 4 shows an exploded perspective view of a capacitive sensor in accordance of another embodiment.

The sensor 70 of FIG. 4 permits simultaneous temperature measurement as well as fluid monitoring. In this particular example, the sensor 70 includes substrates 72, 74, 76, electrodes 78, 80, 82 sandwiched between substrates 72, 74 and electrodes 84, 86 sandwiched between substrates 74, 76. Electrodes 78, 82 are configured for sensing the intrinsic property of the fluid from the measured impedance whereas electrodes 84, 86 are configured for sensing the temperature of the fluid. Electrode 80, which is grounded, is interposed between and about electrodes 78, 82. As previously discussed, the electrodes 78, 82 for monitoring a dielectric constant change in the fluid include complementary pairs of parallel fingers, e.g., 78a and 82a, 78b and 82b, etc, extending along a portion of the length of the substrate 72, whereas the temperature sensing circuitry comprises resistor circuitry formed by electrodes 84, 86 and disposed between insulating layers 74, 76.

Optionally, the above-noted sensors may include additional components such as heater circuitry, a lead gettering layer, and/or the like.

The electrodes are preferably fabricated from a conductive material. More preferably, the electrodes are fabricated from metals such as platinum, palladium, gold, osmium, rhodium, iridium, ruthenium, zirconium, yttrium, cerium, calcium, aluminum, and the like, as well as alloys, oxides, and combinations comprising at least one of the foregoing metals.

With respect to the size and geometry of the sensing electrodes, e.g., 12, 16, 32, 36, 58, 62, 64, 68, 78, 82, they are configured to provide the desired capacitance with an electric field that extends a desired distance away from the surface of the sensor. The distance between parallel pairs of fingers, (e.g., 12a and 16a) together with the geometry of the interposed guard electrode (e.g., 14), determines the distance that the electrical field penetrates into the fluid of interest. Preferably, the distance between pairs of electrode fingers is less than or equal to about 2 millimeters.

Electrodes can be formed using conventional techniques such as sputtering, chemical vapor deposition, screen printing, and stenciling, among others, with screen printing electrodes onto appropriate green tapes generally preferred due to simplicity, economy, and compatibility with a subsequent co-fired process.

The substrates, e.g., 20, 38, 40, 52, 54, 56, 72, 74, 76, serve to mechanically support the electrodes in a known relationship with respect to the fluid to be sensed. The non-conductive substrates preferably comprise a dielectric material such as a ceramic, glass, silica, or a similar material that is capable of inhibiting electrical communication and providing physical protection to the electrodes from the fluid to be sensed. In the event more than one substrate is employed, e.g., sensors 10, 30, 50, 70, it is preferred that each substrate comprise a material having substantially similar coefficients of thermal expansion, shrinkage characteristics, and chemical compatibility in order to minimize, if not eliminate, delamination and other processing problems. In a preferred embodiment, each substrate is fabricated from high purity alumina, (e.g., greater than or equal to about 96 weight % (wt %) alumina) and preferably, flux material. The substrates may preferably comprise greater than or equal to about 80 wt % alumina and less than or equal to 20 wt % flux material, with greater than or equal to about 90 wt % alumina and less than or equal to about 10 wt % flux material more preferred, and greater than or equal to about 96 wt % alumina and less than or equal to about 4 wt % flux material even more preferred based upon the total weight of the substrate composition. The composition of the flux material can be one or more oxides such as silica, lanthanum oxide, alumina, boron oxide, yttria, and the like, as well as combinations comprising at least one of the foregoing flux materials. An exemplary flux material composition comprises, by weight, about 47.5% silica, about 22.5% lanthanum oxide, about 22.5% alumina, about 5% boron oxide and about 2% yttria, based upon the total weight of the flux material.

The substrates shown in FIGS. 1–4 generally have an elongated rectangular shape and are designed for vertically mounting in a container or tank. However, depending on the desired application, other shapes, e.g., rounded, multi-sided and the like, and configurations, e.g., contoured surfaces, ribbon-like surfaces and the like, may be preferred. The thickness of the substrate should be sufficient to support the electrodes, preferably provide handling capabilities, and be environmentally stable for its end application. In this regard, the substrate should be able to tolerate vibrations, heat and the like.

Figure 5:
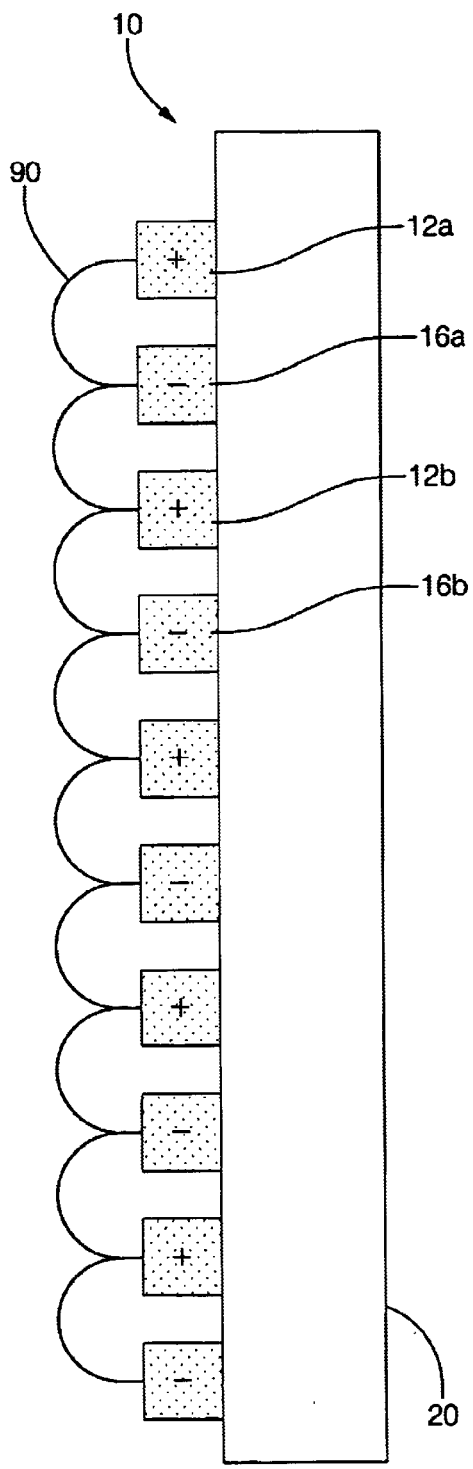
FIG. 5 shows cross sectional side elevation views of the capacitive sensors shown in FIG. 1.
Figure 6:
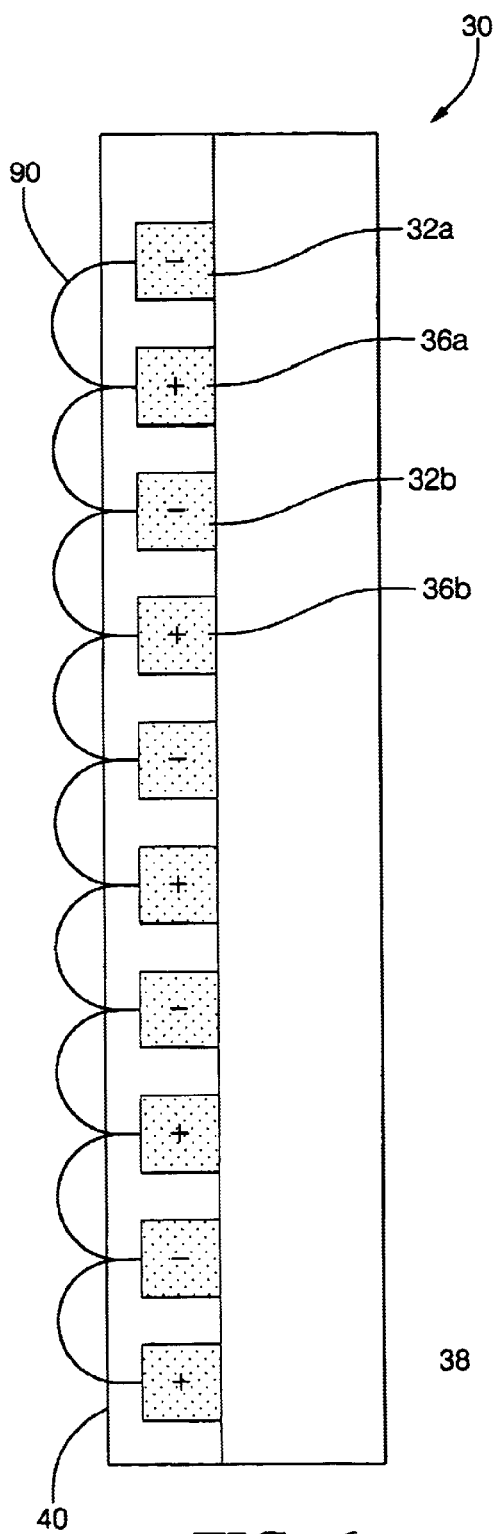
FIG. 6 shows cross sectional side elevation views of the capacitive sensors shown in FIG. 2.

FIGS. 5 and 6 show a side cross-sectional view of sensor 10 and sensor 30, respectively. In operation, a voltage applied to, for example, electrode 12 causes an electric field 90 which induces a charge on both the electrode 14, which is grounded, and on the counter electrode 16, which is maintained at approximately ground potential. The distance between complementary electrode finger pairs, e.g., 12a and 16a, as well as the dimensions of the guard electrode 14, determines the distance that the electrical field 90 penetrates into the fluid of interest.

Figure 7:
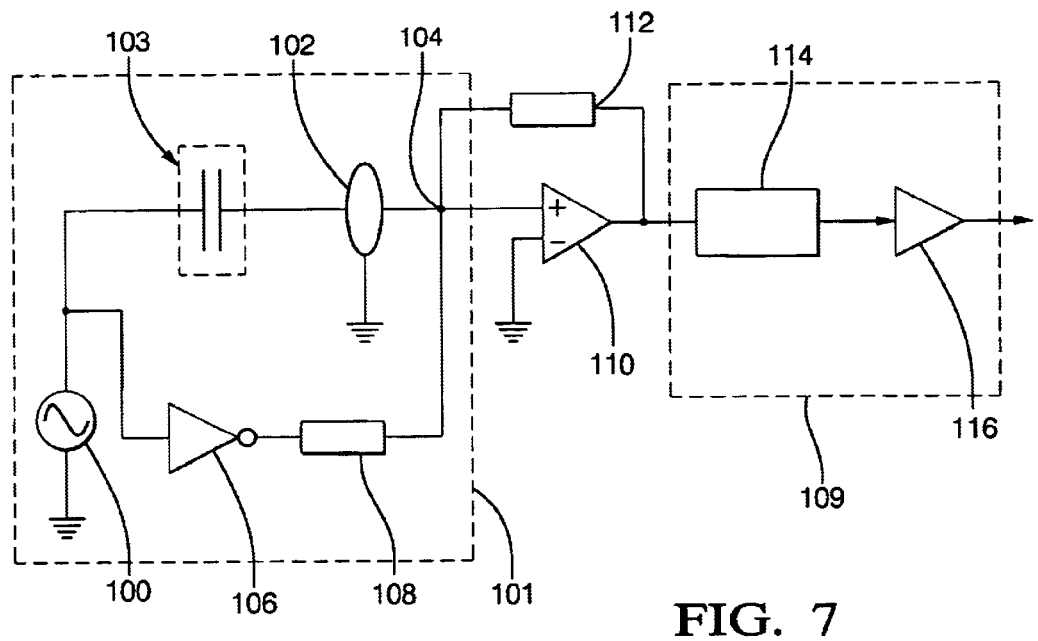
FIG. 7 shows a block circuit diagram for converting capacitance to an output signal.

FIG. 7 shows a block circuit diagram for converting capacitance detected by the sensor to an output signal for use in detecting a change in fluid properties. An oscillating voltage source 100 is applied to a source circuit 101. The source circuit includes a sensor 103, (e.g., 10, 30, 50, 70) which produces an attenuated current signal upon application of the oscillating voltage 100. A ground shield electrode 102 is disposed between the electrodes to minimize parasitic capacitance. The source circuit 101 further includes an analog inverter 106 and a balance impedance 108. The oscillating voltage source 100 is fed through the analog inverter 106 and balance impedance 108 to produce a current having a known value. The balance impedance is set to null the output at a predetermined capacitance. For example, the balance impedance can be based on the known capacitance with pure gasoline in fluid communication with the sensor. The current signal produced in this portion of the circuit is combined with the attenuated circuit signal produced by the sensor at junction 104. If the attenuated signal and current from the balance impedance 108 cancel, there is no change in the dielectric of the fluid from the predetermined condition. In contrast, a detectable signal is produced if there is a change in the dielectric constant of the fluid, e.g., the presence of contaminants, additives or the like. The signal is then fed through an output circuit 109. The output circuit includes an operational amplifier 110 with current feedback impedance 112 and provides amplification to the signal. The amplified signal is then passed through an AC/DC converter 114 to a DC amplifier 116 to produce an output signal that is proportional to changes in the impedance of the fluid.

Advantageously, the capacitive sensor does not require a gap between electrode substrates. Accordingly, the sensors do not exhibit the gap problems noted in the prior art, e.g., manufacturing difficulties, fluid flow effects, etc. Moreover, the use of metal oxide materials such as alumina for the structural components used in the fabrication of the sensor advantageously overcomes the non-linear behavior temperature effects noted with the use of plastic components. Sensors with the foregoing metal oxide structure have shown minimal temperature sensitivity. Use of a grounded guard electrode, e.g., 14, 34, 60, 66, 80, between the source and detection electrodes eliminates slow drifts in the output that would otherwise occur from high dielectric constant materials, such as water, that might be adsorbed into the substrate and cause a change in its dielectric constant, i.e., a source of error. The use of the guard electrode makes the sensor responsive primarily to bulk fluid properties and not to fluid at or near the sensor surface.

EXAMPLE 1

In this example, a capacitive sensor was fabricated from a green ceramic tape comprising 96% by weight alumina powder and a 4% by weight mixture of $SiO_2$, $La_2O_3$, $B_2O_5$, $Y_2O_3$. The tape was prepared by a doctor blade method from an alumina slurry. The sensor comprises (5) five layers of stacked alumina tape. The outer surfaces of the stacked alumina tape were screen-printed using platinum ink with parallel digital finger type of electrodes. Nineteen (19) pairs of digital electrode were formed on each surface. A temperature sensing circuit was screen-printed using platinum ink on one of the surfaces of the third layer. Four contact pads were also formed, i.e., two for the capacitance electrodes and two for the temperature sensing circuitry. The alumina tape was then thermally laminated, cut into shape and fired at 1,450° C. for 2 hours. The dimensions of the sensor include a thickness of 0.81 millimeters (mm), a length of 20 mm, and a width of 10 mm. The capacitance in air using the sensor measured at 10 kilohertz (KHz) was 13.58 picoFarads (pF). Upon immersion in gasoline the capacitance value increased to 15.54 pF. The capacitance after the addition of 10% ethanol in the gasoline increased the capacitance to 16.94 pF. As shown by this example, by monitoring the capacitance of a fluid the sensor can be used to distinguish changes in the fluid dielectric properties.

EXAMPLE 2

In this example, a capacitive sensor was formed in accordance with Example 1. A 65 micrometer layer of alumina in the form of a green tape was laminated onto each surface containing the electrodes. The capacitance of air measured by the sensor at 10 KHz increased to 26.45 pF. The capacitance of gasoline measured by the sensor increased to 28.21 pF whereas capacitance after addition of 10% ethanol to the gasoline increased to 29.08 pF. Therefore, by monitoring the capacitance of a fluid, the sensor can be used to distinguish changes in the fluid dielectric properties.

FIG. 8 illustrates a sensor generally designated by reference numeral 200. The sensor 20Q includes six electrodes 210, 212, 214, 216, 218, and 220 deposited onto a major surface 236 of a substrate 234. The electrodes are configured to include complementary parallel finger pairs, e.g., (224 and 226) and (230 and 232). Each of the electrodes 210, 212, 218, and 220 includes at least two fingers extending from a major portion (222 for electrode 210, 238 for electrode 212, 240 for electrode 218, and 228 for electrode 220) respectively, toward the opposing electrode mica portion respectively. In other words, electrodes 210 and 220 are a pair and electrodes 212 and 218 are a pair. For example, Fingers 232 extend from major portion 228 toward major portion 222 The Fingers 224, 226, 230, and 232 are preferably disposed substantially parallel to each other and more preferably, substantially perpendicular to the main portions 222, 228, 240 and 238. Electrode 214, which is grounded, is interposed between and about electrodes 210 and 220 without physically contacting either electrode. Electrode 216, which is grounded, is interposed between and about electrodes 240 and 238 without physically contacting either electrode.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A sensor comprising:

a substrate consisting essentially of a non-conductive material;

a first electrode, and a second electrode disposed on a first surface of the substrate, wherein the first electrode comprises a first major portion traversing a length of the substrate and a finger extending from the major portion, wherein the second electrode comprises a second major portion traversing the length of the substrate and a finger extending from the second major portion, wherein the frat electrode finger extends toward the second electrode major portion and the second electrode finger extends toward the first electrode major portion and is substantially parallel to the first finger to form a capacitive region; and a third electrode connected to a ground, wherein the third electrode is interposed between and about the first and second electrodes.

2. The sensor according to claim 1, further comprising a second substrate disposed on the first and second electrodes, wherein the first and second substrates are free from any gaps therebetween.

3. The sensor according to claim 1, further comprising a fourth electrode and a fifth electrode disposed on a second surface of the substrate, wherein the fourth electrode comprises a fourth major portion traversing a length of the substrate and a finger extending from the fourth major portion, wherein the fifth electrode comprises a fifth major portion traversing the length of the substrate and a finger extending from the fifth major portion, wherein the fourth electrode finger extends toward the fifth electrode major portion and the fifth electrode finger extends toward the fourth electrode major portion and is substantially parallel to the first finger; and a sixth electrode connected to a ground, wherein the sixth electrode is interposed between and about the fourth and fifth electrodes.

4. The sensor according to claim 1, further comprising a fourth electrode and a fifth electrode disposed on the first surface of the substrate, wherein the fourth electrode comprises a fourth major portion traversing a length of the substrate and a finger extending from the fourth major portion, wherein the fifth electrode comprises a fifth major portion traversing the length of the substrate and a finger extending from the fifth major portion, wherein the fourth electrode finger extends toward the fifth electrode major portion and the fifth electrode finger extends toward the fourth electrode major portion and is substantially parallel to the first finger; and a sixth electrode connected to a ground, wherein the sixth electrode as interposed between and about the fourth and fifth electrodes.

5. The sensor according to claim 1, wherein the non-conductive material comprises alumina, silica, glass, and combinations comprising at least one of the foregoing materials.

6. The sensor according to claim 1, wherein first electrode finger is separated from the second electrode finger by a distance less than or equal to about 2 millimeters.

7. A sensor for measuring a characteristic of a fluid, the sensor comprising:

a first, a second and a third ceramic substrate;

a first capacitive sensor sandwiched between the first and second substrates comprising a first electrode, a second electrode and a third electrode, wherein a portion of the first and second electrodes form complementary parallel finger pairs and wherein the third electrode is grounded and is interposed between and about the first and second electrodes and;

a second capacitive sensor sandwiched between the second and third substrates comprising a fourth electrode, a fifth electrode and a sixth electrode, wherein a portion of the fourth and fifth electrodes form complementary parallel finger pairs, and wherein the sixth electrode is grounded and is interposed between and about the fourth and fifth electrodes; and circuitry means connected to the first and second capacitive sensors for producing an output signal based on an electrical field generated by the finger pairs.

8. The sensor according to claim 7, wherein the first, second and third ceramic substrates comprise greater than or equal to about 96% by weight alumina.

9. The sensor according to claim 7, wherein the sensor is free from any gaps between substrates.

10. The sensor according to claim 7, wherein the substrates comprise a substantially planar surface.

11. The sensor according to claim 7, wherein the substrates comprise a contoured surface.

12. The sensor according to claim 7, wherein the substrate comprises a material selected from the group consisting of alumina, silica, ceramic, glass, lanthanum oxide, boron oxide, yttria, and combinations comprising at least one of the foregoing materials.

13. A system for detecting a change in fluid properties, the system comprising:
a power supply;
a source circuit including a sensor, wherein the sensor comprises a substrate consisting essentially of a non-conductive material; a first electrode, and a second electrode disposed on a first surface of the substrate, wherein the first electrode comprises a first major portion traversing a length of the substrate and a finger extending from the major portion, wherein the second electrode comprises a second major portion traversing the length of the substrate and a finger extending from the second major portion, wherein the first electrode finger extends toward the second electrode major portion and the second electrode finger extends toward the first electrode major portion and is substantially parallel to the first finger; and a third electrode connected to a ground, wherein the third electrode is interposed between and about the first and second electrodes; and
an output circuit comprising amplification means for amplifying a differential signal to produce an output signal that is proportional to a change in an impedance property of a fluid.

14. A process for measuring the capacitive properties of a fluid comprises:
attaching a sensor to a fluid container, wherein the sensor comprises a substrate consisting essentially of a non-conductive material; a first electrode, and a second electrode disposed on a first surface of the substrate, wherein the first electrode comprises a first major portion traversing a length of the substrate and a finger extending from the major portion, wherein the second electrode comprises a second major portion traversing the length of the substrate and a finger extending from the second major portion, wherein the first electrode finger extends toward the second electrode major portion and the second electrode finger extends toward the first electrode major portion and is substantially parallel to the first finger; and
a third electrode connected to a ground, wherein the third electrode is interposed between and about the first and second electrodes;
applying an oscillating voltage source to the first electrode;
generating an electrical field between the first electrode finger and the second electrode finger, wherein the electrical field extends into the fluid and
monitoring a current passing to the ground from the second electrode.

15. The process according to claim 14, wherein the sensor further comprises a fourth electrode and a fifth electrode disposed on a second surface of the substrate, wherein the fourth electrode comprises a fourth major portion traversing a length of the substrate and a finger extending from the fourth major portion, wherein the fifth electrode comprises a fifth major portion traversing the length of the substrate and a finger extending from the fifth major portion, wherein the fourth electrode finger extends toward the fifth electrode major portion and the fifth electrode finger extends toward the fourth electrode major portion and is substantially parallel to the fist finger; and a sixth electrode connected to a ground, wherein the sixth electrode is interposed between and about the fourth and fifth electrodes.

16. The process according to claim 14, wherein the sensor further comprises a fourth electrode and a fifth electrode disposed on the first surface of the substrate, wherein the fourth electrode comprises a fourth major portion traversing a length of the substrate and a finger extending from the fourth major portion, wherein the fifth electrode comprises a fifth major portion traversing the length of the substrate and a finger extending from the fifth major portion, wherein the fourth electrode finger extends toward the fifth electrode major portion and the fifth electrode finger extends toward the fourth electrode major portion and is substantially parallel to the first finger; and a sixth electrode connected to a ground, wherein the sixth electrode is interposed between and about the fourth and fifth electrodes.

17. The process according to claim 14, wherein the sensor further comprises a second substrate disposed onto the first and second electrodes and the substrate, wherein the sensor is free from any gap between the second substrate and the substrate.

* * * * *